United States Patent
Yarchoan et al.

(10) Patent No.: US 6,509,321 B1
(45) Date of Patent: Jan. 21, 2003

(54) TREATMENT OF KAPOSI'S SARCOMA WITH IL-12

(75) Inventors: Robert Yarchoan, Bethesda, MD (US); James M. Pluda, Gaithersburg, MD (US); Kathleen Wyvill, Upper Marlboro, MD (US); Jill Lietzau, Columbia, MD (US); Gene M. Shearer, Bethesda, MD (US); Ellen Feigal, N. Potomac, MD (US); Giovanna Tosato, Bethesda, MD (US); Richard Little, Washington, DC (US); Matthew L. Sherman, Newton, MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/672,448

(22) Filed: Sep. 29, 2000

Related U.S. Application Data

(62) Division of application No. 09/396,931, filed on Sep. 15, 1999.
(60) Provisional application No. 60/100,416, filed on Sep. 15, 1998.

(51) Int. Cl.[7] .................. A01N 43/04; A61K 38/21; A61K 45/00
(52) U.S. Cl. .................. 514/44; 514/23; 424/85.1; 424/85.2
(58) Field of Search .............. 424/85.2, 85.1; 514/44, 23

(56) References Cited

U.S. PATENT DOCUMENTS

| | | | |
|---|---|---|---|
| 5,571,515 A | 11/1996 | Scott et al. | 424/208.1 |
| 5,665,347 A | * 9/1997 | Metzger et al. | 424/85.2 |
| 5,922,685 A | * 7/1999 | Rakhmilevich et al. | 514/44 |

FOREIGN PATENT DOCUMENTS

| | | |
|---|---|---|
| EP | 441900 | 11/1989 |
| WO | WO 90/05147 | 11/1989 |
| WO | WO 94/01139 | 7/1993 |

OTHER PUBLICATIONS

Verma et al.; Gene Therapy . . . ; Nature; vol. 389; pp. 239–242, 1997.*
Ross et al.; Gene Therapy in the United States . . . ; Human Gene Therapy; vol. 7; pp. 1781–1790, Sep. 1996.*
Crystal; Transfer of Genes to Humans . . . ; Science; vol. 270; pp. 404–409, 1995.*
Blau et al.; Gene Therapy–A novel form of drug delivery; New Eng. J. Med.; vol. 333, No. 18; pp. 1204–1207, Nov. 1995.*
Angiolillo et al., Human interferon–inducible protein 10 is a potent inhibitor of angiogenesis in vivo, J Exp Med 182: 155–162 (1995).
Brunda et al., Antitumor and antimetastatic activity of interleukin 12 against murine tumors, J Exp Med 178: 1223–1230 (1993).
Clerici et al., Changes in interleukin–2 and interleukin–4 production in asymptomatic, human immunodeficiency virus–seropositive individuals, J Clin Invest 91: 759–765 (1993).
Clerici et al., Restoration of HIV–specific cell–mediated immune responses by interleukin–12 in vitro, Science 262: 1721–1724 (1993).
Cohen, Science 259: 1691–1692 (1993).
Foli et al., Effects of the Th1 and Th2 stimulatory cytokines interleukin–12 and interleukin–4 on human immunodeficiency virus replication, Blood 85: 2114–2123 (1995).
Fynan et al., PNAS USA 90: 11478–11482 (1993).
Kobayashi et al., J. Exp. Med. 170: 827 (1989).
Maggi et al., Ability of HIV to promote a TH1 to TH0 shift and to replicate preferentially in TH2 and TH0 cells, Science 265: 244–248 (1994).
Mosmann et al., Two types of murine helper T cell clone. I. Definition according to profiles of lymphokine activities and secreted proteins, Journal of Immunology 136: 2348–57 (1986).
Romagnani et al., Human TH1 and TH2 subsets: doubt no more, Immunol. Today 12: 256–257 (1991).
Scott et al., The role of T–cell subsets and cytokines in the regulation of infection, Immunology Today 12: 346–348 (1991).
Scott, IL–12: initiation cytokine for cell–mediated immunity, Science 260: 496–497 (1993).
Sher et al., Role of T–cell derived cytokines in the down-regulation of immune responses in parasitic and retroviral infection, Immunol. Reviews 127: 183–204 (1992).
Trinchieri, Interleukin–12: a cytokine produced by antigen-presenting cells with immunoregulatory functions in the generation of T–helper cells type 1 and cytotoxic lymphocytes, Blood 84: 4008–4027 (1994).
Voest et al., Inhibition of angiogenesis in vivo by interleukin 12, J Nat'l Cancer Inst 87: 581–586 (1995).
Wolff et al., Biotechniques 11: 474–485 (1991).

* cited by examiner

*Primary Examiner*—Hankyel T. Park
*Assistant Examiner*—Stacy S. Brown
(74) *Attorney, Agent, or Firm*—Finnegan, Henderson, Farabow, Garrett & Dunner, L.L.P.

(57) ABSTRACT

Methods are provided for using IL-12 to treat Kaposi's sarcoma (KS), particularly AIDS-associated KS.

12 Claims, No Drawings

TREATMENT OF KAPOSI'S SARCOMA WITH IL-12

This is a divisional application of application Ser. No. 09/396,931, filed Sep. 15, 1999, and claims the benefit of U.S. provisional application No. 60/100,416, filed Sep. 15, 1998, both of which are incorporated herein by reference.

FIELD OF THE INVENTION

The present invention relates generally to treatment of Kaposi's sarcoma ("KS"), particularly AIDS-associated KS, with interleukin-12 ("IL-12").

BACKGROUND OF THE INVENTION

The reports in 1981 of Kaposi's sarcoma (KS) associated with AIDS in homosexual males increased interest in this heretofore uncommon neoplastic disease. It soon became apparent that the KS associated with this epidemic was more fulminate than either the classical or the endemic African forms, generally following a rapidly progressive course. In the setting of AIDS, KS can progress to involve visceral organs and, particular pulmonary KS, is not infrequently a cause of death. Moreover, aggressive cutaneous and lymphatic involvement is often a cause of substantial morbidity. At one point, KS was the second most common AIDS-defining illness. However, as the epidemic has matured, and the definition of what constitutes AIDS has been modified, the incidence of KS as the initial AIDS-defining illness in patients has fallen. However, the absolute number of KS cases continues to rise and KS now frequently develops after patients have had another AIDS-defining illness. The distribution of KS in the setting of AIDS is not uniform among all groups at risk for HIV infection, with the majority of cases occurring in white, male homosexuals. In fact, KS is seven times more common in homosexual or bisexual men (27.3%) than in all other AIDS patients combined (3.9%).

There is no curative therapy for KS at present. While there is some evidence to suggest that antiretroviral therapy may, under certain circumstances, delay or even partially reverse the development of KS, this tumor generally requires specific therapy. Numerous modalities have been tried with various results. Interferon alpha has been useful in obtaining good responses particularly in patients with disease limited to the skin and with T4 cell counts that are above 200/mm$^3$. However, this is not a cure, and interferons can have toxicities that often overlap with those of AZT and can interfere with antiretroviral therapy. At present, studies are ongoing to try to administer interferons with various antiretroviral therapies. Localized KS lesions are usually treated with radiation therapy. More aggressive or visceral lesions are generally treated with cytotoxic chemotherapy. Chemotherapy of KS with various agents has resulted in tumor responses that may be substantial; however, these responses tend to be incomplete, temporary, and are often short-lived. Also, many of these agents are associated with significant myelosuppression and immunosuppression, and patients often cannot tolerate therapy for long periods of time. In addition, treatment with many of these agents may predispose patients to the development of opportunistic infections (OI).

Although the pathogenesis of KS is not completely understood, there is a substantial body of evidence to show that the process of angiogenesis is central to the initiation and propagation of KS lesions. Kaposi's sarcoma-derived cells cultured in vitro have been shown to secrete a variety of autocrine and paracrine growth factors, including some with potent angiogenic including basic fibroblast growth factor (bFGF), vascular endothelial growth factor (VEGF), platelet-derived growth factor (PDGF), and interleukin-1 (IL-1). Many of these same factors, in addition to others such as scatter factor (SF) and HIV-1 Tat, have also been shown to stimulate in vitro growth of KS-derived spindle cells. These same KS cells, when inoculated subcutaneously into nude mice, were found to be able to induce the growth of a KS-like lesion that was of mouse tissue origin. In addition, similar lesions were induced by the co-inoculation of bFGF and Tat as well as Tat and heparin. Thus it would appear that KS-derived spindle cells secrete factors that, alone or in combination with Tat, are capable of inducing the formation of KS-like lesions. In addition, the growth and development of these lesions in mice can be inhibited by the systemic administration of agents or compounds with anti-angiogenic activity such as tissue inhibitor of metalloproteinase-2 (TIMP-2) or tecogalan.

There are also data implicating endothelial cells as the cell of origin for the KS spindle cell. Cultured endothelial cells take on a spindle morphology when exposed to cytokines released in vitro by activated T lymphocytes, including many of the cytokines that induce in vitro KS-derived spindle cell proliferation. In addition, these endothelial cells also become sensitive to the in vitro proliferative effects of Tat in a manner similar to that of KS-derived spindle cells.

The initial stimulus or factor that initiates the proposed cytolkine cascade leading to the development of KS is not known. However, there is a growing body of literature suggesting that a herpes-like virus, tentatively named Kaposi's sarcoma herpes virus (KSHV) or human herpes virus-8 (HHV-8) may be involved. There are reports that this virus appears to be present in or associated with KS lesions from HIV-infected as well as classical and African KS at a much greater frequency than in patients without KS, although it has been reported in a number of other disease such as body cavity lymphomas and Castleman's disease. In addition, there is a recent report that KSHV is present in the flat endothelial cells lining vascular spaces of KS lesions as well as in typical KS spindle cells. Thus, although the exact mechanisms and steps associated with the development of KS is not known, it is clear that angiogenesis is central to the overall pathogenesis of this disease.

Studies have shown that CD4positive T-lymphocytes can be divided into two major groups: T helper type 1 cells ($T_H1$) cells that produce interleukin-2 (IL-2) and interferon-gamma, and T helper type 2 cells ($T_H2$) cells that mainly produce interleukin4 (IL-4), interleukin-5 (IL-5), interleukin-6 (IL-6), and interleukin-10 (IL-10)[1-4]. In general, $T_H1$ cells mediate cellular, type-1 immune responses while $T_H2$ cells are involved in humoral type-2 immune responses. In the setting of HIV infection, there is a decrease in interleukin-2 production and other $T_H1$-mediated type-1 reactions with an enhancement of $T_H2$-mediated type-2 reactions, and this shift of immune responses away from type-1 predominance is felt to be a central feature of HIV infection[5,6].

In summary, AIDS-associated KS is a serious neoplastic disorder associated with AIDS that can cause significant morbidity and even death. Treatment for this disorder at present is not optimal, and there is a definite need for newer agents that are better tolerated. As noted above, there is evidence that neovascularization is important in the development of KS. For this reason, it has been hypothesized that inhibition of angiogenesis may potentially benefit patients with KS. As will be described below, interleukin 12 (IL-12) has been shown to have potent antiangiogenic activity and is able to substantially stimulate $T_H1$ immune responses.

Interleukin-12 (IL-12) is a cytokine that has been found to enhance the proliferation of activated T and natural killer (NK) cells; to enhance cytotoxic T and NK cell activity; and to induce interferon-gamma (IFN-γ) production[7]. Also, IL-12 has demonstrated anti-tumor and anti-metastatic activity in preclinical models[8]. In addition, IL-12 has been shown to potentiate the growth and differentiation of $T_H1$ cells while inhibiting $T_H2$ activity[9]. This effect of T helper differentiation by IL-12 has also been found to restore HIV-specific cell-mediated immune responses ex vivo in T cells from HIV-infected patients[10].

More recently, Voest and colleagues have reported that IL-12 is a potent antiangiogenic agent[11]. They further found that the anti-angiogenic activity of IL-12 was mediated through induction of IFN-γ. Subsequently, Angiolillo and colleagues reported that human interferon-inducible protein 10 (IP-10), a chemokine induced by IFN-γ, is a potent inhibitor of in vivo angiogenesis[12]. Therefore, it appears that the antiangiogenic activity of IL-12 may be through its induction of local IFN-γ production with subsequent upregulation of IP-10 production. Thus, IL-12 has been shown to possess potent antiangiogenic activity in vivo as well as to selectively enhance $T_H1$ activity.

Foli and associates have recently reported the effects of IL-12 on in vitro HIV replication[13]. They showed that IL-12 induced in vitro replication of HIV in prestimulated, fresh peripheral blood mononuclear cells (PBMC) as determined by the production of HIV p24 antigen over 7 days of culture. This IL-12-induced HIV replication was not attributable to induction of IL-1, IL-2, tumor necrosis factor-alpha or -beta and was associated with a selective loss of the CD4 subset in stimulated cultures. However, IL-12 had little or no effect on HIV replication in monocyte/macrophages. Finally, they showed that the IL-12-induced increase in HIV replication could be inhibited by the dideoxy-nucleosides AZT, ddI, and ddC[13]. Thus, there is a possibility that systemically administered IL-12 may increase HIV replication in infected patients, particularly in the absence of antiretroviral therapy.

There have been numerous Phase I and Phase II trials administering IL-12 intravenously or subcutaneously employing a variety of doses and schedules. There were a number of toxicities noted. These included fever and constitutional symptoms; nausea, vomiting anorexia, diarrhea, stomatitis, dyspepsia, and guiac positive stools; transient decreases of leukocyte, lymphocyte, neutrophil, and platelet counts with anemia and occasional increases in PT and PTT; transient elevations of serum glucose values and less frequently hyperglycemia; dose-dependent elevations of SGOT, SGPT, alkaline phosphatase, and bilirubin; dyspnea; hematuria, proteinuria, elevated serum creatinine and blood urea nitrogen, and oliguria; confusion, anxiety, dizziness, insomnia, hypotonia, nervousness, somnolence, and tremor; hypotension and some peripheral edema; erythema and pruritis at the site of subcutaneous injections that resolved spontaneously; and increases in thyroid stimulating hormone (TSH).

Six patients died while receiving IL-12; 4 deaths were from disease progression while 2 were attributable to the IL-12. The two patients whose death was felt to be related to IL-12 were both enrolled on Phase II trials treating patients with renal cell carcinoma with 500 ng/kg of IL-12 intravenously daily×5 days every 3 weeks. One patient died on cycle 1 day 10 as the result of a lower gastrointestinal bleed, and the other died on cycle 1 day 23 due to multiple organ failure. It ultimately was determined that the toxicity profile of IL-12 was highly schedule dependent and that the dose administered in the Phase II trial was too high for that schedule. In particular, earlier Phase I studies had utilized a single dose of IL-12 with a delay before multiple doses were given, while the Phase II trial did not utilize this earlier single dose. There are data to suggest that through an as yet undetermined mechanism, this initial dose of IL-12 induced a sort of tolerance that reduced toxicity to subsequent doses.

There are data on single-dose, placebo-controlled Phase I trials administering IL-12 subcutaneously to HIV-infected patients with either 100–300 CD4 cells/mm$^3$ or 301–500 CD4 cells/mm$^3$. The dose levels studied were 3, 10, 30, 100, 300, and 1000 ng/kg. The maximally tolerated dose (MTD) was found to be 300 ng/kg on the basis of toxicity observed at the 1000 ng/kg dose (fatigue, stomatitis, aminotransferase elevations, and hyperbilirubinemia). There were no clinically significant changes in CD4 or CD8 cell counts or plasma viremia (measured by a branched-chain DNA assay) in any subject. There were, however, transient increases in interferon-gamma and neopterin levels seen in patients receiving doses greater than 100 ng/kg.

A Phase I/II double-blind, randomized, placebo-controlled, multicenter, dose-escalating study of IL-12 in HIV-infected patients having 100 to 500 CD4 cells/mm$^3$ was initiated in November, 1995. Interleukin-12 is being administered by subcutaneous injection twice a week for 12 weeks. The dose levels to be studied are 30, 100, 300, and 500 ng/kg/injection of IL-12. Twenty-four patients will be enrolled in each dose cohorts (18 receiving IL-12 and 6 receiving placebo) to ensure that there will be 20 evaluable patients who complete at least 4 weeks of study drug administration. A total of 26 patients have been enrolled at the 30 ng/kg dose level. Four patients have been withdrawn from the study for non-safety-related reasons. Thirteen patients have completed 12 weeks of therapy. The 30 ng/kg dose has been well tolerated. To date, no serious adverse events related to study drug administration or dose-limiting toxicities have been reported. Dose escalation to the 100 ng/kg dose level has occurred and 10 patients have been enrolled at this dose level.

It would, therefore, be desirable to provide treatment for KS by administration of IL-12.

SUMMARY OF THE INVENTION

The present invention provides for a method for treating Kaposi's sarcoma in a mammalian subject, which method comprises administering to the subject a therapeutically effective amount of IL-12 or a biologically active fragment or subunit thereof.

In other embodiments, the present invention provides for a method for inhibiting angiogenesis in a lesion associated with Kaposi's sarcoma in a mammalian subject, which method comprising administering to the subject a therapeutically effective amount of IL-12 or a biologically active fragment or subunit thereof.

In preferred embodiments, the subject treated has AIDS. In other preferred embodiments, IL-12 is administered as a protein or in the form of DNA encoding IL-12.

In still other preferred embodiments, IL-12 protein is administered at a dose of from 100–1000 ng/kg of subject body weight, preferably at a dose selected from the group consisting of 300, 500, 625, and 750 ng/kg of subject body weight, and most preferably at a dose of 300 ng/kg of subject body weight.

Other aspects and advantages of the present invention will be apparent upon consideration of the following detailed description of preferred embodiments thereof.

DETAILED DESCRIPTION OF THE INVENTION

Interleukin-12 (IL-12), originally called natural killer cell stimulatory factor, is a heterodimeric cytokine described, for example, in M. Kobayashi et al., 1989, *J. Exp. Med.* 170: 827. IL-12 can be purified from natural sources, produced by chemical synthesis, or preferably produced by recombinant DNA techniques, for example by the expression and isolation of IL-12 protein in recombinant host cells as described in detail in International Patent Application WO90/05 147, published May 17, 1990 (also European Patent Application No. 441,900), incorporated by reference herein. The DNA and amino acid sequences of the 30 kD and 40 kD subunits of the heterodimeric human IL-12 are provided in the above recited international application and in U.S. Pat. No. 5,571, 515, incorporated by reference herein. Research quantities of recombinant human and murine IL-12 are also available from Genetics Institute, Inc., Cambridge, Mass.

As used herein, "interleukin-12" and "IL-12" refer to interleukin-12, its individual subunits, fragments thereof which exhibit IL-12 adjuvant activity, polynucleotides encoding IL-12, and functional equivalents of "interleukin-12" and "IL-12".

A therapeutically effective amount of IL-12 is an amount that when administered results in (1) diminution of KS symptoms, including without limitation a decrease in the number, recurrence, spread, or size of one or more KS lesions, or (2) a reduction in angiogenesis in one or more existing KS lesions or in the formation of new KS lesions. The amount of IL-12 administered to the host will vary depending on a variety of other factors, including the antigen(s) employed, the size, age, body weight, general health, sex, and diet of the host, the time or duration of administration, and the particular qualities of the KS lesions being treated. As one example, a therapeutically effective amount of IL-12 polypeptide is desirably between about 10 ng to about 1000 ng (preferably about 100 ng to about 750 ng, or about 100 ng to about 300 ng, or about 300 ng to about 500 ng, or about 500 ng to about 750 ng) of IL-12 polypeptide per kg patient body weight. Preferred doses are 100 ng/kg, 300 ng/kg, 500 n/kg, 625 ng/kg, and 750 ng/kg. The effective amount for any particular patient will be readily defined by balancing the efficacy and toxicity of the IL-12 administration. Adjustment and manipulation of established dose ranges are well within the ability of those skilled in the art.

The IL-12 can be administered to a host in a variety of ways. The routes of administration include without limitation intradermal, transdermal (for example, by slow-release polymers), intramuscular, intraperitoneal, intravenous, subcutaneous, oral, aural, epidural, anal or vaginal (for example, by suppositories), and intranasal routes. Any other convenient route of administration can be used, for example, infusion or bolus injection, or absorption through epithelial or mucocutaneous linings. Particularly prefered routes of administration are those which patients can conveniently administer to themselves in in-home settings, such as without limitation intradermal, transdermal (for example, by slow-release polymers), intravenous, subcutaneous, oral, aural, epidural, anal or vaginal (for example, by suppositories), or intranasal routes of administration, or absorption through epithelial or mucocutaneous linings. In addition, the IL-12 can be administered in combination with other components or biologically active agents, such as any of a variety of anti-viral agents (for example, nucleoside analog reverse transcriptase inhibitors, non-nucleoside reverse transcriptase inhibitors, and/or protease inhibitors) or any of a variety of anti-neoplastic or chemotherapeutic agents (for example, acyclic nucleoside phosphonates, Adriamycin, bleomycin, and/or vincristine, either individually or in combination), or other biologically active agents such as tretinoin. Other pharmaceutically acceptable components may also be administered in combination with IL-12, for example surfactants such as glycerides, excipients such as lactose, carriers diluents, and vehicles. If desired, certain sweetening, flavoring, and/or coloring agents can also be added.

Further, IL-12 can be administered by in vivo expression in the host of polynucleotides encoding IL-12. The polynucleotides, preferably in the form of DNA, may be delivered to the patient for in vivo expression of IL-12. So-called 'naked DNA' may be used to express IL-12 in vivo in a host. (Cohen, J., 1993, *Science* 259: 1691–1692; Fynan, E. et al., 1993, *PNAS USA* 90: 11478–11482; and Wolff, J. A. et al., 1991, *Biotechniques* 11:474–485 describe similar uses of 'naked DNA', all incorporated by reference herein.)

Still other modes of delivering IL-12 to the patient in the form of polynucleotides encoding them are known to those of skill in the art and may be employed rather than administration of IL-12 polypeptides, as desired. For example, polynucleotides encoding IL-12 may be administered as part of a vector or as a cassette containing the sequences encoding IL-12 operatively linked to a promoter sequence. (For example, see International Patent Application PCT WO94/ 01 139, published Jan. 20, 1994 and incorporated by reference herein.) Briefly, the DNA encoding IL-12 protein or desired fragments thereof may be inserted into a nucleic acid cassette. This cassette may be engineered to contain, in addition to the IL-12 sequence to be expressed, other optional flanking sequences which enable its insertion into a vector. This cassette may then be inserted into an appropriate vector downstream of a promoter, an mRNA leader sequence, an initiation site, and other regulatory sequences capable of directing the replication and expression of that sequence in vivo. Additional regulatory sequences may be inserted downstream of the coding sequence to be expressed. This vector permits in vivo expression of the IL-12 polypeptides within the host.

Patent and literature references cited herein are incorporated by reference as if fully set forth.

The following examples illustrate embodiments of the present invention, but are not intended to limit the scope of the disclosure.

EXAMPLE 1

Clinical Treatment of AIDS-Associated KS with IL-12

As of the time of this filing, the following clinical protocol has been and is being conducted in human subjects at the National Cancer Institute. Despite the use of present or future tense in the text which follows, reported procedures have been and are actually being conducted.

Eligibility Assessment and Enrollment

Patients are evaluated for eligibility according to the following criteria for inclusion or exclusion.

Inclusion Criteria

Patients with HIV infection and biopsy-confirmed Kaposi's sarcoma (KS) who have disease that is evaluable by non-invasive methods and a life expectancy of >3 months.

All patients must also have serum antibodies to HIV as measured by ELISA and western blot.

Patients must be ambulatory with a Karnofsky performance status of at least 70.

All patients must be receiving a stable dose of antiretroviral therapy consisting of a combination of two or more of the following: AZT, ddI, ddC, 3TC, d4T, saquinavir, ritonavir, indinavir, a non-nucleoside reverse transcriptase inhibitor, or another protease inhibitor. Treatment with other therapies is allowed as long as it is considered a community standard of care. The patients have to be on this regimen for 4 weeks prior to IL-12 therapy.

Patients must be at least 18 years old and capable of giving informed consent.

All patients of child-fathering or -bearing potential must agree to use medically accepted birth control measures while on study and for 2 months afterward.

A total bilirubin≦3.7 mg/dl with direct fraction≦0.2 mg/dl and indirect fraction of ≦3.5 mg/dl in patients for whom these abnormalities are felt to be due to protease inhibitor therapy.

Exclusion Criteria

Pregnancy, or the possibility of becoming pregnant during drug administration. All female patients of child-bearing potential must have a negative pregnancy test within 2 weeks of entry onto the study. All patients of child-fathering or -bearing potential must agree to use medically accepted birth control measures while on study and for 2 months afterward. In addition, lactating/breast-feeding patients will not be allowed on study. In this regard, it should be noted that the major risk of breast-feeding is transmission of HIV to the offspring, with the risk due to the study drug being additional.

Patients with pulmonary or acutely life-threatening KS which may be responsive to other therapies will be ineligible. In addition, patients with actively bleeding or critically located KS lesions may, if in the judgment of the Principal Investigator or Study Chairperson these lesions pose an immediate risk to the patient, be ineligible.

Any one of the following hematologic abnormalities:
1. A Hb<9.0 gm/dl or transfusion within 1 month prior to entry;
2. An absolute neutrophil count (ANC)<750 cells/mm$^3$;
3. A platelet count<75,000 cells/mm$^3$;
4. APTT or PT>120% of control A history of hepatic cirrhosis or present hepatic dysfunction with:
1. Total bilirubin>2 m/dL
2. AST/GOT>2.5 times the upper limit of normal Serum creatinine>1.5 mg/dL and an estimated or measured creatinine clearance<60 mL/min.

Clinically significant autoimmune disease (i.e. disease caused by production of antibodies and/or an immunologic response by the body against itself, such as systemic lupus erythematosis), and/or rheumatologic disease.

Active, gross gastrointestinal bleeding or uncontrolled peptic ulcer disease.

A history of inflammatory bowel disease.

Past or present history of malignant tumors other than KS, with the exception of patients who have been in complete remission for ≧1 year from the discontinuation of their therapy, or have completely resected basal cell carcinoma or in situ squamous cell carcinoma of the cervix.

Evidence of a severe or life-threatening infection with bacterial, viral, fungal, protozoal, or parasitic pathogens within 2 weeks of entry onto the study. In general, patients who have had a fever of >39° C. or greater within the 10 days prior to entry onto the study will be ineligible, unless it is evident that this is not due to a severe underlying infection.

Patients with any other abnormality, except lymphopenia or direct manifestations of KS, that would be scored as a grade 3 toxicity (see Table 1 below).

Known hypersensitivity to IL-12 or other compounds that are known to cross-react with IL-12.

Patients should have not previously received IL-12 for any reason. Also, treatment within the last 6 months with suramin; treatment within the last 3 weeks with any cytotoxic chemotherapeutic agent or regimen (6 weeks for mitomycin C or nitrosoureas), interferon, other systemic anti-KS therapy or regimen, radiation therapy, or local treatment (such as intralesional injections); treatment within the last 6 weeks with cytokines or bone marrow stimulating factors other than erythropoietin (Epo); treatment within the last 2 months with systemic glucocorticoid steroids at doses sufficient to affect the immune response. In general, this would mean an equivalent of more than 20 mg of prednisone for more than 1 week. Replacement glucocorticoid therapy would be allowed. Androgen or mineralocorticoid therapy is discouraged but allowed.

Inability to give informed consent or unwillingness to refrain from unprotected sexual contact or other activities that might result in re-infection with HIV.

Any medical condition that, in the opinion of the Principal Investigator or Study Chairperson, would preclude the inclusion of a patient onto this research study.

Research Eligibility Evaluation

Pretreatment evaluation will be performed within 14 days of starting therapy and will include a complete history, review of systems, and physical examination, with particular attention to the neurologic exam and any neurologic complaints. If the patient is to begin treatment within 48 hours of screening, the following studies need not be repeated at the time of enrollment. Screening studies will include:

HIV serology

Acute care panel

Hepatic panel

Mineral panel

CPK, uric acid, amylase, lipase, LDH

CBC, diff (automated lymphocyte count), retic count, ESR

APTT, PT, thrombin time (TT), fibrinogen

Urinalysis

Pregnancy test (if female)

EKG

Chest x-ray

FACS-including CD4, CD8, RA and RO T cells (Four 10 cc green-topped tubes to SIAC, Frederick, Md., scheduled in advance, which must be picked up before 12 noon. A simultaneous CBC and automated differential must be drawn.)

Red-topped tube to Frederick, Md. for storage

Yellow top tube for storage for plasma HIV-1-RNA-PCR (send to SIAC, Frederick, Md.)

Patient Registration

Each patient will be discussed with the Principal Investigator (Dr. Yarchoan) or the Study Chairperson (Dr. Pluda). Once it has been determined that a patient qualifies, informed consent will be obtained from the patient, as documented by a signed statement of informed consent approved by the NCI-IRB. The physician caring for the patient must register the patient with the Medicine Branch protocol office by calling Orkand Co. In addition, Orkand Co. is to be called at the same number at the time that a patient is taken off protocol. Prior to the administration of the first dose, a history and general physical examination and negative pregnancy test, where appropriate, will be recorded, along with an evaluation of the patient's KS.

Maximum number of patients: 55

Study Implementation

This study is designed as a pilot trial administering 3 successively higher doses of IL-12 to patients with HIV-associated KS. Information regarding the tolerability of each dose will be collected, as well as preliminary information regarding the activity of IL-12 when administered to such patients. Also, data will be collected regarding the immunologic and virologic effects of IL-12 when administered to patients with HIV-associated KS.

Patients will receive IL-12 twice weekly subcutaneously (SC). Successive cohorts will receive successively higher doses of IL-12; 100 ng/kg/dose, 300 ng/kg/dose, 500 ng/kg/dose, 625 ng/kg/dose, and 750 ng/kg/dose. However, unless a dose is modified in response to a toxicity, a given patient will receive a constant dose of IL-12 with no intra-patient dose escalations. Patients may receive IL-12 initially for up to 12 weeks. Previously, patients achieving a stable or better clinical KS response after 12 weeks could receive up to an additional 16 weeks of therapy for a total of 28 weeks of treatment. Since beneficial antitumor or immunologic effects have been observed and are continuing after 28 weeks of therapy, an amendment has been sought to prolong the period of drug administration to 18 months (one and one half years). Additional patients may be treated at the highest dose tolerated in order to explore the activity of IL-12 in patients with HIV-associated KS.

Initially, from 3 to 6 patients will be entered at each dose level. Up to an additional 10 patients may be enrolled at the highest tolerable dose to confirm the tolerability of this dose level and to obtain exploratory information on the activity of IL-12 in this patient population. Up to 3 of the original 6 patients at each dose level not completing the initial 4 weeks of therapy for reasons other than drug toxicity may be replaced (for a maximum total patient accrual of 55 patients). Patients should not have the presence of pulmonary, critically located, or actively bleeding KS lesions.

The dose level will be escalated in successive cohorts of 3 patients so long as no dose-limiting toxicity is observed (see the "Toxicity Criteria" section below). If 1 instance of dose-limiting toxicity is observed among the initial 3 patients treated at a dose level, an additional 3 patients must be treated at that dose level with no further dose-limiting toxicity in order that dose escalation may proceed. If 2 instances of dose-limiting toxicity are observed at a dose level, the highest tolerated dose has been surpassed. It is desirable that at least 6 patients total be treated at the previous level to assure its tolerability.

The highest tolerated dose will be defined as the highest dose level administered as part of the protocol where 0 of 6 or 1 of 6 patients (e.g. $\leq 1/6$ of patients) experience dose-limiting toxicity (see the "Toxicity Criteria" section below for definition). Upon determination of the highest tolerated dose level, up to an additional 10 patients may be enrolled on this dose level in order to better define the tolerability and toxicity of this dose level and to preliminarily explore the activity of IL-12 in patients with HIV-associated KS. It is possible that, after a review of data from this or other studies administering IL-12, accrual of additional patients to a dose level below the highest tolerated dose may be warranted. If this occurs, an amendment will be made to the protocol to allow additional patients to be enrolled on dose levels below the highest tolerated dose.

Drug Administration

Patient evaluation and drug administration will be performed in the outpatient setting. However, admission for evaluation of complications may be required if medically necessary. Patients will receive their initial dose of IL-12 in the NCI Outpatient Cancer Center (day hospital) and be observed for 1 hour following administration. Subsequent doses of IL-12 will be administered in the NCI Outpatient Cancer Center, the patient's home physician's office, or at home by a nurse or other health care-trained professional.

A single dose of IL-12 will be administered subcutaneously (SC) twice a week, at least 3 days apart, to 3 successive cohorts of patients. The doses of IL-12 administered will be:

| Level 1 | 100 ng/kg/dose two times a week |
| Level 2 | 300 ng/kg/dose two times a week |
| Level 3 | 500 ng/kg/dose two times a week |
| Level 4 | 625 ng/kg/dose two times a week |
| Level 5 | 750 ng/kg/dose two times a week |

Three to six patients will be entered initially on each dose level.

IL-12 will be administered to patients within each dose level for up to 12 weeks. Up to 3 patients at each dose level who are removed from study prior to completion of 4 weeks of therapy for reasons other than drug toxicity may be replaced, at the discretion of the Principal Investigator or Protocol Chairperson.

After at least 3 patients have completed the first 4 weeks of IL-12 administration without developing a dose-limiting toxicity (see the "toxicity Criteria" section below for definition) at a particular dose level, subsequent patients may be enrolled on the next highest dose level.

Upon determination of the highest tolerated dose level, up to an additional 10 patients may be enrolled on this dose level in order to better define the tolerability and toxicity of this dose level and to preliminarily explore the activity of IL-12 in patients with HIV-associated KS.

Initially, patients achieving a stable or better clinical KS response after 12 weeks could receive up to an additional 16 weeks of therapy. Since beneficial antitumor or immunologic effects have been observed and are continuing after 28 weeks of therapy, an amendment has been sought to prolong the period of drug administration to 18 months (one and one half years).

An attempt will be made for at least 6 patients receiving the highest tolerable dose to have their IL-12 injections performed immediately adjacent to a cutaneous KS lesion that is not one of the marker lesions (see the "Kaposi's Sarcoma Evaluation" section below for definition of a marker lesion) for a minimum of 4 weeks.

Treatment Modifications

With the exception of lower than grade 4 transaminase elevations (see Table 1 below), patients experiencing a dose-limiting toxicity (see the "Toxicity Criteria" section below for definition) may be retreated at the next lowest dose level (50% of the starting dose for patients on level 1) provided that the toxicity resolves to $\leq$grade 1 within 4 weeks of stopping the drug. Patients whose toxicity fails to resolve within 4 weeks of stopping IL-12 or who have the recurrence of dose-limiting toxicity on a lower dose will be removed from the study. Patients who develop dose-limiting transaminase elevations lower than grade 4 that resolve as above may be retreated at the same dose of IL-12. If the dose-limiting hepatic toxicity recurs and recovers off drug as above, then they would be retreated at the next lowest dose. Patients who develop dose-limiting hepatic transaminase toxicity on this lower dose will be removed from the study.

Patients who develop melena or grossly bloody stools will have their IL-12 held pending appropriate evaluations.

On Study Evaluation

The following baseline studies are performed prior to beginning treatment (if the patient begins treatment within 48 hours of screening, the screening evaluations listed in "Research Eligibility Evaluation" above do not need to be repeated):

Acute care panel

Hepatic panel

Mineral panel

Thyroid function tests (TSH, TT4)

CPK, uric acid, amylase, lipase, LDH, beta-2-microglobulin

CBC, diff (automated lymphocyte count), retic count, ESR

APTT, PT, thrombin time (TT), fibrinogen

Urinalysis

Pregnancy test (if female)

FACS-including CD4, CD8, RA and RO T cells (Four 10 cc green-topped tubes to SIAC, Frederick, Md., scheduled in advance, which must be picked up before 12 noon. A simultaneous CBC and automated differential must be drawn.)

EBV antibody, CMV antibody

Hepatitis B S Ag, Hepatitis B S Ab

Hepatitis C antibody

RBC folate, vitamin $B_{12}$, iron, transferrin, VDRL

Red-topped tube to Frederick, Md. for storage 40 cc of heparinized blood (in green-topped tubes) will be drawn for immunologic testing ($T_H1/T_H2$ profile and IL-2 production in response to mitogens and antigens) (send to Dr. Gene Shearer's lab, room 5A31.)

Up to 20 cc may be drawn for virologic testing, establishment of cell lines, evaluation of hematologic parameters, or other studies that become clinically important during conduct of the trial (If the investigators are interested in studying genetic/familial markers, they will return to the IRB with an amendment to the protocol in order to conduct this research.)

Quantitative immunoglobulin levels, including IgE

Yellow top tube for storage for plasma HIV-1 RNA-PCR (send to SIAC, Frederick, Md.)

Two red top tubes for serum interferon-gamma, IP-10, bFGF, VEGF, and IL-6. Place one of these tubes on ice immediately upon drawing (send to Dr. Yarchoan's lab, room 5A25)

20 cc of urine for bFGF (send to Dr. Yarchoan's lab, room 5A25)

EKG

CXR; CT of chest when possible (CT required when the clinical scenario or CXR results suggest a pulmonary process)

Other studies where indicated to evaluate and measure internal tumor

Biopsy-proven KS is required before a patient can enter on study. (Patients should either bring in the slides of an outside biopsy for review or have a biopsy done during the screening process.) In addition, a biopsy of an easily accessible cutaneous lesion, normal skin, or samples of pleural or ascitic fluid may be obtained for research purposes, such as establishment of cell lines and attempts to identify possible KS-related viruses. Refusal to allow such sampling will not prevent a patient from entering on study.

Kaposi's Sarcoma Evaluation

Baseline whole body photographs will be obtained upon entry into the study. At this time, 5 lesions (hereafter called marker lesions), representative of the patient's disease and, if possible, located on separate areas of the body will be selected. These marker lesions should be lesions that have never been treated with local therapies such as radiation therapy or intralesional injections. Detailed photographs of these lesions will be obtained with a metric rule beside them. The size, color and nodularity of these lesions will be recorded at each clinic visit. If there are a total of more than 50 lesions, from 1–3 representative areas of the body which contain more than 20 KS lesions (also see the "Response Criteria" section below) will be selected. An attempt will be made to distribute the "marker" lesions between the representative areas and the rest of the body. Radiological studies will be performed at entry where clinically indicated. Evaluation of whole body KS lesions will be performed as follows:

Patients will be evaluated at entry to determine whether they have 50 or more lesions.

(1) For patients with 50 or more lesions at entry, between 1 and 3 representative areas will be selected at baseline and these will be used for each subsequent evaluation. Representative areas are sections of the body (e.g. the back, a leg, an arm, etc.) which contain at least 20 KS lesions. The total number of lesions in these representative areas will be counted and a record made of whether they are flat or raised. If, in the course of treatment, a single lesion breaks up into 2 or more smaller lesions (whose area does not extend beyond the boundary of the initial lesion), these lesions will still be counted as single lesions for the purpose of assessing total numbers in defining a response to therapy.

(2) For patients with less than 50 lesions at entry, the total number of lesions will be counted and a record made of whether they are flat or raised.

Treatment Phase and Follow-up

General evaluation. Patients will be evaluated in clinic once a week for the first 6 weeks of therapy, and then every 2 weeks while on study. Evaluation will be made at each clinic visit of subjective symptoms, including headache, nausea, vomiting, diarrhea, abdominal discomfort, appetite, tremors, night sweats, rash, muscle and joint aches, ability to concentrate, paresthesias, and mental and neurological status. Objective signs will include a complete physical examination, weight changes, and fever. Temperatures and weights will be evaluated at each clinic visit.

Evaluation of Kaposi's Sarcoma

Evaluation at each clinic visit: The marker lesions will be measured, and a record made of their size, color, and nodularity at each clinic visit Evaluation every 4 weeks:

(1) The marker lesions will be measured, and a record made of their size, color, and nodularity, and the total number of lesions (if the patient, at baseline, had less than 50 lesions) or the lesions within previously defined representative areas (if the patient had more than 50 lesions) will be counted at the completion of every 4 weeks of treatment as described in the "Kaposi's Sarcoma Evaluation" section, as well as at the end of treatment or whenever a patient comes off study.

(2) Whole body and marker lesion photographs will be obtained at the completion of every 8 weeks of treatment, as well as at the end of treatment or whenever a patient comes off study. Radiological studies, where appropriate, will be repeated every 8 weeks (or more frequently if clinically indicated) as well as at the end of treatment or whenever a patient comes off study.

For patients receiving their IL-12 injections immediately adjacent to a KS lesion, this lesion will be photographed, measured, and a record made of its nodularity and color prior to initiation of therapy. This lesion will be measured and a record made of its nodularity and color at each clinic visit as long as the injections continue to be given adjacent to it, and photographed every 8 weeks or whenever the injections adjacent to it are discontinued, regardless of whether the patient continues to receive IL-12 injected elsewhere.

Laboratory Studies. The following laboratory studies should be obtained at each clinic visit (but not more than once per week, unless clinically indicated):

CBC with differential, ESR reticulocyte count

APTT, PT, fibrinogen

Acute panel, hepatic panel, mineral panel

Urinalysis

Tests obtained every 4 weeks:

CBC with differential, ESR, reticulocyte count

APTT, PT, fibrinogen

Acute panel, hepatic panel, mineral panel

Thyroid function tests (TSH, TT4)

Red-topped tube to Frederick, Md. for storage

Urinalysis, CPK, amylase, LDH, beta-2-microglobulin, uric acid

Two Red top tube for serum bFGF, VEGF, interferon-gamma, IP-10, and IL-6. Place one of these tubes on ice immediately upon drawing. (send to room 5A25)

20 cc of urine for bFGF (send to room 5A25)

FACS-including CD4, CD8, RA and RO T cells (Four 10 cc green-topped tubes to SIAC, Frederick, Md., scheduled in advance, which must be picked up before 12 noon. A simultaneous CBC and automated differential must be drawn)

Up to 20 cc of blood may optionally be drawn for virologic testing, establishment of cell lines, evaluation of hematologic parameters, or other studies that become clinically important during conduct of the trial (If the investigators are interested in studying genetic/familial markers, they will return to the IRB with an amendment to the protocol in order to conduct this research.)

Yellow top tube for storage for plasma HIV-1-RNA-PCR (send to SIAC, Frederick, Md.)

Tests obtained at weeks 4, 8, 12, and 24:

40 cc of heparinized blood (in green-topped tubes) will be drawn for immunologic testing ($T_H1/T_H2$ profile and IL-2 production in response to mitogens and antigens) (send to Dr. Gene Shearer's lab, room 5A31).

Tests at completion of study:

All required blood tests done every 4 weeks.

A chest x-ray will be performed every 6 weeks while on therapy.

Patients may have biopsies of easily accessible cutaneous lesions obtained as clinically indicated. In addition, at entry to the protocol or at any time during the course of the study, a biopsy of a representative lesion, of uninvolved skin or samples of pleural or ascitic fluid may be obtained for research purposes, such as establishment of cell lines and attempts to identify possible KS-related viruses. Additionally, non-KS related cutaneous lesions may be obtained for the same studies. If biopsies of visceral KS lesions are done for clinical purposes, samples may also be utilized for these research purposes. Biopsies of appropriate KS lesions may be obtained to determine if a representative lesion has resolved pathologically. Refusal to undergo such biopsies will not prevent a patient from being entered onto or continuing the trial.

Other tests may be obtained as clinically indicated. Tests may be rescheduled to the closest possible day without constituting a protocol violation (e.g., Federal holidays, or unforeseen circumstances such as travel difficulties).

Concurrent Therapies

See the "Supportive Care" section below for a discussion of antiretroviral therapy. Every effort should be made to give only medications that are clearly indicated for a specific medical purpose during the trial. It is particularly important to avoid systemic glucocorticoid steroid administration if at all possible, as their use may exacerbate KS. In addition, drugs that are likely to affect KS lesions, immunologic parameters, or HIV-8/KSHV should be avoided where possible. Any other treatments, medications, biological products, or blood products, including over-the-counter medications, imported drugs, or street drugs that the patient has taken in the month prior to starting therapy will be recorded. Any readily available information regarding exposure to nephrotoxic, marrow toxic, immunomodulatory, or hepatotoxic drugs or agents will be recorded. With the exception of exclusionary drugs noted above, the patients will in general be kept on the drugs that they were taking prior to entry unless a change in the drug regimen is medically warranted. Patients will not receive any immunomodulatory agents or, as stated below, therapies for their KS. Patients may receive erythropoietin (Epo) or, if absolutely required, granulocyte-colony stimulating factor (G-CSF) as per standard medical practice. The use of other cytokines will not be allowed. Finally, careful attention should be paid to the potential for drug interactions between the protease inhibitors and other drugs the patient may be taking.

Off Study Criteria

Treatment will be discontinued for any of the following reasons:

The occurrence of dose limiting toxicity. However, patients experiencing a dose-limiting toxicity (see "Toxicity Criteria" section for definition) may be retreated at the next lowest dose level (50% of the starting dose for patients on level 1) provided that the toxicity resolves to baseline or grade 1 (whichever represents a more abnormal value) within 2 weeks of stopping the drug. Patients whose toxicity fail to resolve within 2 weeks of stopping IL-12 or who have the recurrence of dose-limiting toxicity on a lower dose will be removed from the study.

Patients who develop an absolute neutrophil count (ANC) <500 cells/mm$^3$ may continue to receive IL-12 and have G-CSF added, 300 µg three times a week (tiw), until the ANC is ≧750 cells/mm$^3$. If the ANC does not increase to ≧750 cells/mm$^3$ while receiving the G-CSF, then the IL-12 will be stopped and the G-CSF continued. IL-12 may then be restarted at the next lowest dose level (50% of the starting dose for patients on level 1) if the ANC rises to ≧750 cells/mm³ within 2 weeks of stopping the drug. Patients whose ANC fails to increase to ≧750 cells/mm³ within 2 weeks of stopping IL-12 or who have the recurrence of dose-limiting toxicity on a lower dose will be removed from the study. An attempt will be made to taper and discontinue the G-CSF as long as the ANC remains ≧750 cells/mm³.

The onset of a life-threatening infection after the patient has been enrolled onto the study. In such a case, the patient may resume receiving IL-12, at the discretion of the Principle Investigator or Study Chairperson, after completion of the therapy for the infection providing this period is not greater than 4 weeks. However, those patients who have previously shown evidence of improvement on IL-12 and who are off IL-12 for >4 weeks, may, at the discretion of the discretion of the Principle Investigator or Study Chairperson, may be put back on IL-12 within 2 weeks of the resolution of the illness.

Generalized debilitation of mental incapacitation that would render the patient unable to give informed consent.

Any other potential adverse reaction or event deemed sufficiently serious by the Principal Investigator or Study Chairperson to warrant discontinuation of therapy.

Therapy may be discontinued upon patient non-compliance with the protocol, at the discretion of the Principal Investigator or Study Chairperson.

Pregnancy of a patient.

Inability to take a combination of 2 or more antiretroviral agents as stated in the "Supportive Care" section below.

Progression of disease and disease that is severe enough to, in the opinion of the Principal Investigator or Study chairperson, require cytotoxic therapy. Interleukin 12 may, as with other inhibitors of angiogenesis, be cytostatic and thus result in either stable disease or a decrease in the rate of progression of KS. Therefore, patients with disease that, although progressive by the definition in the "Response Criteria" section below, is not severe or life threatening may, after discussion with the patient and the Principal Investigator or Protocol chairperson, continue receiving IL-12.

Therapy may be discontinued at the request of the patient or at the discretion of the Principal Investigator or Study Chairperson.

Post-Study Evaluation

Patients will be seen for a follow-up evaluation 4 weeks after completion of treatment. If any drug toxicity remains at the follow-up evaluation, patients will be followed as medically indicated until the toxicity stabilizes. Evaluation will be made of subjective symptoms, including headache, nausea, vomiting, diarrhea, abdominal discomfort, appetite, tremors, night sweats, rash, muscle and joint aches, ability to concentrate, paresthesias, and mental and neurological status. Objective signs will include a complete physical examination, weight changes, and fever. Temperatures and weights will be evaluated at each clinic visit.

Laboratory studies

CBC with differential, ESR, reticulocyte count

APTT, PT, fibrinogen

Acute panel, hepatic panel, mineral panel

Thyroid function tests (TSH, TT4)

Red-topped tube to Frederick for storage

Urinalysis, CPK, amylase, LDH, beta-2-microglobulin, uric acid

Two Red top tube for serum bFGF, VEGF, interferon-gamma, IP-10, and IL-6. Place one of these tubes on ice immediately upon drawing (send to room 5A25)

20 cc of urine for bFGF (send to room 5A25)

FACS-including CD4, CD8, RA and RO T cells (Four 10 cc green-topped tubes to SIAC, Frederick, Md., scheduled in advance, which must be picked up before 12 noon. A simultaneous CBC and automated differential must be drawn)

Up to 20 cc of blood may optionally be drawn for virologic testing, establishment of cell lines, evaluation of hematologic parameters, or other studies that become clinically important during conduct of the trial.

Yellow top tube for storage for plasma HIV-1-RNA-PCR (send to SIAC, Frederick, Md.)

40 cc of heparinized blood (in green-topped tubes) may be drawn for immunologic testing ($T_H1/T_H2$ profile and IL-2 production in response to mitogens and antigens) (send to Dr. Gene Shearer's lab, room 5A31).

Supportive Care

Medications may be administered as clinically indicated, or at the discretion of the Principal Investigator or Study Chairperson, with the following exceptions:

Specific therapy for KS during the first 12 weeks of the study. After this period, occasional painful or disfiguring lesions may, on rare occasions, be treated with localized therapy at the discretion of the Principal Investigator or Study Chairperson and concurrence of the IND holder. However, the patient must continue to have at least 5 evaluable KS lesions. However, every attempt possible will be used to avoid such therapy.

Any medications noted in the exclusion criteria with the exception of short-term courses of corticosteroids.

All patients must be receiving a stable dose of antiretroviral therapy consisting of a combination of two or more of the following: AZT, ddI, ddC, 3TC, d4T, saquinavir, ritonavir, indinavir, a non-nucleoside reverse transcriptase inhibitor or another protease inhibitor, either alone or in combination, for 4 weeks prior to IL-12 therapy and while on study. Treatment with other therapies is allowed as long as it is considered a community standard of care. In general, every attempt possible should be made not to change the patient's antiretroviral therapy during the protocol, as the effect (if any) of IL-12 on viral load is of interest. However, changes in doses may be made if they are medically warranted. Also, if medically indicated, a patient may be switched between antiretroviral agents or regimens after entry on study as long as they continue to receive a combination of 2 or more agents. Patients requiring discontinuation of their antiretroviral therapy for any reason will be removed from study.

All patients should receive a therapeutic multivitamin with minerals, and low vitamin $B_{12}$ or folate levels should be corrected with specific vitamin replacement therapy. Patients should also be on prophylactic therapy for opportunistic infections, as is medically indicated.

Data Collection and Evaluation

Data will be collected by the members of the Retroviral Diseases Research Team. Dr. James M. Pluda, the Protocol Chairperson, will be immediately responsible for oversight of the protocol.

Response Criteria

The evaluation of the response of KS to an agent or regimen is difficult to grade by means of commonly used oncologic definitions. However, in an effort to standardize the evaluation of therapy against KS, the AIDS Clinical Trial Group Oncology Committee has devised a set of staging and response definitions for KS. We will use a modification of these criteria to assess the response of patients with KS to the administration of IL-12. It should be noted that there is some observer variability in the evaluation of the number, size, nodularity, and color of lesions, and this must be taken into account when measurements are interpreted.

For evaluation of less than complete responses in patients with more than 50 lesions at entry, only the previously selected 1–3 representative areas which contain at least 20 lesions will be considered. However, complete responses still require the absence of any detectable disease over the entire body (i.e. not confined to the representative areas).

Complete Response (CR): The absence of any detectable residual disease, including tumor-associated edema, persisting for at least 4 weeks. In patients in whom pigmented macular skin lesions persist after apparent CR, biopsy of at least one representative lesion is required to document the absence of malignant cells. In patients known to have bad visceral disease, an attempt at restaging with appropriate endoscopic or radiographic procedures should be made. If such procedures are medically contraindicated, the patient may be classified as having a clinical CR.

Partial Response (PR): No net increase in the number of lesions (noting, as described in the "Kaposi's Sarcoma Evaluation" section, that single lesions which split up into 2 or more smaller lesions during the course of treatment will still be counted as one); no new lesions occurring in previously uninvolved areas of the body; no new visceral sites of involvement or the appearance or worsening of tumor-associated edema or effusions and:

(1) A 50% or greater decrease in the number and/or size of previously existing lesions lasting for at least 4 weeks or
(2) Complete flattening of at least 50% of all previously raised lesions (i.e., 50% of all previously nodular or plaque-like lesions become macular) lasting for at least 4 weeks or
(3) A 50% decrease in the sum of the products of the largest perpendicular diameters of the marker lesions lasting for at least 4 weeks or
(4) A 50% decrease in radiologically measurable visceral lesions as confirmed by a Clinical Center radiologist (generally Dr. Feuerstein) sustained without evidence of regrowth for at least 4 weeks or
(5) Patients who otherwise meet the criteria for a CR but still have residual tumor-associated edema or effusions will be classified as having a PR.

Clinical Complete Response: The absence of any detectable residual disease, including tumor associated edema, persisting for at least 4 weeks. For patients with pigmented macular skin lesions persisting after apparent complete response, a representative lesion has not been biopsied and found to be without disease. For patients with visceral disease, the diagnostic radiologic or endoscopic study should be repeated if not medically contraindicated and found to be negative for evidence of disease.

Progressive Disease: For those criteria that involve measurement of lesions in the clinic, the designation of progression should be made, when feasible, only when the criteria below have been met in two measurements spaced at least 1 week apart.

(1) An increase of 25% or more over baseline in the number of lesions and/or the size (sum of the products of the largest perpendicular diameters) of the marker lesions or
(2) A change in character from macular to plaque-like or nodular of at least 25% of the lesions or
(3) New visceral sites of involvement or progression of visceral disease or
(4) The development of new or increasing tumor-associated edema or effusion that lasts at least 1 week and interferes with the patient's normal activities.

Toxicity Criteria

The NCI Common Toxicity Criteria (CTC) will be used to assess toxicity (see Table 1 below). However, as lymphopenia is nearly a universal finding in late HIV infection, lymphocyte counts will be scored as per the CTC but will not count as a dose-limiting toxicity of IL-12 or as a criteria for stopping therapy.

Grade 4 thrombocytopenia; grade 4 anemia not responsive to erythropoietin; and grade 4 neutropenia not responsive to G-CSF (see the "Off Study Criteria" section above) will be considered dose-limiting. Lymphopenia is a frequent manifestation of HIV infection and will not be used as a dose-limiting toxicity, no matter what the grade.

Grade 2 cardiac and neurologic toxicities will be considered dose-limiting.

Any grade 3 or greater nonhematologic toxicity (excluding those mentioned in the "Toxicity Criteria" section, hyperbilirubinemia, and elevated hepatic transaminase levels) will be considered dose-limiting. For patients with increased bilirubin, a total bilirubin>4.8 mg/mL if the direct bilirubin is >0.3 mg/mL and the indirect bilirubin is >4.5 mg/mL will be considered dose-limiting. For patients with elevated hepatic transaminase levels, a transaminase >500 IU will be considered dose-limiting.

Any grade 3 or greater nonhematologic toxicity (excluding those mentioned in the "Toxicity Criteria" section and hyperbilirubinemia) will be considered dose-limiting. For patients with increased bilirubin, a total bilirubin>4.8 mg/mL if the direct bilirubin is >0.3 mg/mL and the indirect bilirubin is >4.5 mg/mL will be considered dose-limiting.

Visible or visualizable KS lesions that, in the opinion of the Principal Investigator or Protocol Chairperson, undergo necrosis and/or bleeding as a result of a response to treatment with IL-12, will not constitute an adverse event or be considered a drug-related toxicity.

The above toxicities will be considered dose-limiting unless, upon evaluation, the toxicity is found to be probably or definitely due to the patients underlying condition. Patients with AIDS sometimes develop abnormal clinical or laboratory conditions in the absence of therapy (e.g. fever from *Pneumocystis carinii* pneumonia {PCP}). For the sake of the protocol, patients who develop dose-limiting toxicities which, after evaluation, are found to be due to their AIDS, will not be scored as such toward defining the highest tolerated dose. If such toxicity due to AIDS develop within the first 4 weeks of drug administration or a patient elects to drop out of the study during this period, another patient may be entered in their place.

Statistical Considerations

The main objective of the study is to obtain information on the tolerability of IL-12 administered to patients with HIV-associated KS over a range of 5 increasing dose levels and to determine the highest tolerable dose of those administered. From 3 to 6 patients will be entered onto each of the 5 dose levels, and up to 3 patients per dose level may be replaced as specified in the "Study Design" section above. The highest tolerated dose will be defined as the highest dose level administered as part of the protocol where 0 of 6 or 1 of 6 patients experience dose-limiting toxicity. Upon determination of the highest tolerated dose level, up to an additional 10 patients may be enrolled on this dose level in order to better define the tolerability and toxicity of this dose level and to preliminarily explore the activity of IL-12 in patients with HIV-associated KS. Thus, the study would have a maximum accrual of 55 patients. It is possible that, after a review of data from this or other studies administering IL-12, accrual of additional patients to a dose level below the highest tolerated dose may be warranted. If this occurs, an amendment will be made to the protocol to allow additional patients to be enrolled on dose levels below the highest tolerated dose.

Preliminary information will be obtained regarding the activity of IL-12 in patients with HIV-associate KS. As previously stared, the evaluation of the response of KS to an agent or regimen is difficult to grade by means of commonly used oncologic definitions. However, in an effort to standardize the evaluation of therapy against KS, the AIDS Clinical Trial Group Oncology Committee has devised a set of staging and response definitions for KS. Therefore, we will use a modification of these criteria, as delineated in the "Response Criteria" section above, to assess the response of patients with KS to the administration of IL-12. It should be noted that there is some observer variability in the evaluation of the number, size, nodularity, and color of lesions, and this must be taken into account when measurements are interpreted.

To further explore the possible effect of IL-12 on the underlying HIV infection and immunologic function, assessments will be made of changes in viral load (assaying for HIV RNA PCR); the absolute number of CD4 cells; serum and/or urine levels of interferon-gamma, bFGF, VEGF, and IL-6; and $T_H1/T_H2$/subsets and IL-2 production. To assess these changes, the primary comparison will be between the results at week 12 and entry. Non-parametric tests will be used for comparison for exploratory purposes, and adjacent dose-level groups may be combined to increase the power to see a change. Other time points (including week 4) will also be examined and compared with entry.

Subjects from both genders and all racial/ethnic groups are eligible for this study if they meet the eligibility criteria outlined in the "Eligibility Assessment and Enrollment" section above. To date, there is no information that suggests that differences in drug metabolism or disease response would be expected in one group compared to another. Efforts will be made to extend accrual to a representative population, but in this preliminary study, a balance must be struck between patient safety considerations and limitations on the number of individuals exposed to potentially toxic and/or ineffective treatments on the one hand, and the need to explore gender and ethnic aspects of clinical research on the other hand. If differences in outcome that correlate to gender or to ethnic identity are noted, accrual may be expanded or a follow-up study may be written to investigate those differences more fully. As a practical matter, it should be noted that for reasons that are not completely understood, KS is relatively rare in females with HIV infection, and it is thus expected that the vast majority of patients recruited onto the study will be male.

The estimated annual accrual for this trial is 24 patients/year (2 patients/month). Therefore, if the protocol were to accrue the maximum number of patients (55), the estimated length of time to enroll those 55 patients would be ~2.5 years.

Research Ethics

The investigational nature and objectives of this trial, the procedures and treatments involved and their attendant risks and discomforts, potential benefits, and potential alternative therapies will be carefully explained to the patient, and a signed informed consent document will be obtained.

Data Reporting

The Cancer Treatment Evaluation Program (CTEP) of the NCI will monitor this protocol, and data will be supplied to the Clinical Trials Monitoring Service every 2 weeks using the DCT Case Report Form or an acceptable magnetic tape format. Toxicities which occur should be reported to CTEP as stipulated in Attachment 1 of the CTEP Investigator's Handbook. Specifically, all life threatening (Grade 4) toxicities which may be due to drug administration, and all fatal events should be reported to the Investigational Drug Branch (phone: 230-2330, FAX: 230-0159) within 24 hours. A written report within 10 working days should be sent (using the CTEP ADE forms to:

Investigational Drug Branch

P. O. Box 30012

Bethesda, Md. 20824

The first occurrence of any new toxicity, regardless of grade, should be reported to the drug monitor within the Investigational Drug Branch within 24 hours. An ADE form may be required. In addition, all ADE's will be reported to the IRB, NCI within 10 working days.

Pharmaceutical Information

IL-12 (NSC# 672423) is an investigational agent manufactured by Genetics Institute. The IND will be held and drug supplied by CTEP, DCTDC, NCI.

Formulation. This trial will use recombinant human IL-12 (rhIL-12) drug product that will be supplied as a lyophilized powder in 5 mL vials under mild vacuum. Each vial will contain 50 μg of rhIL-12. The label attached to each rhIL-12 vial will contain the appropriate information, including product name and amount, lot number, storage conditions, name of sponsor, and proper regulatory caution. Vials of rhIL-12 are intended for single use only. Sterile water for injection (WFI) will be supplied to reconstitute the lyophilized drug product. BACTERIOSTATIC WFI SHOULD NOT BE USED TO RECONSTITUTE rhIL-12.

Storage. The rhIL-12 lyophilized drug product must be stored in a secured refrigerated facility at 2° C. to 8° C. The WFI may be stored at controlled room temperature. Dosing solutions are stable in the vial after reconstitution for two (2) hours at 2° C. to 8° C. Unit doses in the syringes may be kept at controlled room temperature and must be used within four (4) hours of preparation.

Preparation. The rhIL-12 drug product will be supplied as a lyophilized powder in a 5 mL vial containing 50 μg rhIL-12. The dose of study drug, rhIL-12, will be calculated using the weight in kilograms (kg) of the subject. Patients will be weighed at each clinic visit and a new dose will be calculated to determine the dose of study drug to be given if the patient's weight has changed ±5% from baseline. Lyophilized drug product will be reconstituted with either 5 mL or 1 mL of sterile WFI. Reconstitution with 5 mL of WFI will provide a 10 μg/mL dosing solution to be used for the 100 ng/kg dose level. Reconstitution with 1 mL of WFI will provide a 50 μg/mL dosing solution to be used for the 300 ng/kg and all higher dose levels. To reconstitute rhIL-12, WFI is injected into the vial through the stopper. It may be necessary to remove some of the air from the vial to facilitate the 5 mL dilution. For the 5 mL dilution, it is recommended that first approximately 2 mL WFI be added to the powder vial. Some air should be removed with the SAME syringe before the additional 3 mL is added. The vial is then gently rolled to dissolve the powder. Reconstitution will be complete in approximately one (1) minute. After reconstitution, any vial with discoloration or particulate matter should not be used. The tables below provide examples of dose volumes based on the subject's weight ranging from 40–100 kg for the planned study dose levels of 100 ng/kg and all levels $\geq$300 ng/kg employing one of the two dosing solutions. The table specifies the dosing solution (10 or 50 μg/mL) to be used for preparation of study drug doses.

| rhIL-12 Dosage Group | Volume of WFI Needed for Reconstitution of 50 μg vial | Final Concentration of Dosing Solution |
|---|---|---|
| 100 ng/kg | 5.0 mL | 10 μg/mL |
| $\geq$300 ng/kg | 1.0 mL | 50 μg/mL |

Sample calculation for a 65.4 kg patient to receive the 300 ng/kg dose level:

Reconstitution with 1 mL WFI will provide 50 μg/mL dosing solution=50,000 ng/ml

Total dose=65.4 kg×300 ng/kg=19,620 ng

Volume Injected=Total Dose÷concentration=19,620 ng÷50,000 ng/mL=0.39 mL

Administration Procedures. Dosing will be calculated based on actual body weight in kg as indicated in the "Drug, Administration" section above. The study drug will be administered by subcutaneous (SC) injection. No more than 2 mL should be injected subcutaneously as a single shot.

Drug Accountability and Drug Ordering. Drug may be requested by completing a Clinical Drug Request (NIH-986) and mailing it to the Drug Management and Authorization Section, DCTDC, NCI, EPN Room 707, Bethesda, Md. 20892 or faxing it to (301) 480-4612. For questions call (301) 496-5725.

Drug Inventory Records. The investigator, or responsible party designated by the investigator, must maintain a careful record of the inventory and disposition of all drugs received from DCTDC, using the NCI Drug Accountability Record Form. (See the NCI Investigators Handbook for Procedures for Drug Accountability and Storage.)

EXAMPLE 2

Results of Clinical Treatment of AIDS-Associated KS With IL-12

Fifteen (15) patients were enrolled pursuant to the protocol outlined in Example 1. Patients were treated at 100 ng/kg (5 patients), 300 ng/kg (6 patients) and 500 ng/kg (4 patients) per the protocol. Median CD4 count for the enrolled patients was 201 cells/mm$^3$ (range 17–602 cells/mm$^3$. Median viral load for the enrolled patients was 2384 copies/mL (range 0–156,996 copies/mL). The stage of KS progression in the enrolled patients was to scored using the ACTG TIS staging system as follows:

| | |
|---|---|
| good progression | 0 patients |
| poor prognosis | 15 patients |
| $T_1$ | 12 patients |
| $I_1$ | 7 patients |
| $S_1$ | 11 patients |

Enrolled patients had received prior treatment as follows:

| | |
|---|---|
| None | 1 patient |
| Chemotherapy | 9 patients |
| Interferon | 3 patients |
| Local Therapy | 2 patients |
| Experimental Therapy | 10 patients |

Treated patients exhibited the following laboratory toxicities (as defined in the protocol of Example 1):

| Toxicity | Grade 2 | Grade 3 | Grade 4 |
|---|---|---|---|
| Leukopenia | 8 | 3 | 0 |
| Neutropenia | Not Assessed | 6 | 4 |
| SGPT | 0 | 3 | 0 |
| SGOT | 3 | 2 | 0 |
| T. Bilirubin | 4 | 1 | 0 |
| Glucose | 4 | 0 | 0 |

Four (4) patients received G-CSF; three continued IL-12 without further neutropenia, while the fourth was intolerant of G-CSF and unable to continue IL-12 therapy.

The treated patients exhibited the following clinical toxicities (as defined in the protocol of Example 1):
  Syndrome of fever, sweating, fatigue, headache
    Onset with initiation of therapy
    Spontaneous resolution within 1 to 2 weeks of continued therapy
  Injection site
    Itching
    Minimal discomfort As of the filing of this application, treated patients had demonstrated the following clinical outcomes:
  100 ng/kg dose level: 5 patients
    1 presumed CNS toxoplasmosis week 1
    3 progression weeks 2, 4, and 4
    1 stable disease completed 26 weeks of therapy
  300 ng/kg level: 6 patients
    1 dose-limiting hepatic toxicity week 3
    2 partial responses
      1 neutropenia with intolerance to G-CSF week 22
      1 continues at week 13+
    3 stable continue at weeks 25+, 19+, and 15+
  500 ng/kg level: 4 patients
    4 stable continue at weeks 9+, 8+, 7+, and 4+

These data demonstrate that IL-12 is well-tolerated in KS patients and that IL-12 treatment produces a clinical response in treatment of KS.

REFERENCES

1. Mosmann T R, Cherwinski H, Bond M W, Giedlin N L A, Coffman R L. Two types of murine helper T cell clone. I. Definition according to profiles of lymphokine activities and secreted proteins. J Immunol 1986; 136:2348–57.
2. Scott P, Kaufman S H E. The role of T-cell subsets and cytokines in the regulation of infection. Immunol. Today 1991; 12:346–8.

3. Sher A, Gazzinelli R T, Oswald I P, et al. Role of T-cell derived cytokines in the downregulation of immune responses in parasitic and retroviral infection. Immunol. Reviews 1992; 127:183–204.
4. Romagnani S. Human TH1 and TH2 subsets: doubt no more. Immunol Today 1991; 12:256–7.
5. Clerici M, Hakim F T, Venzon D J, et al. Changes in interleukin-2 and interleukin4 production in asymptomatic, human immunodeficiency virus-seropositive individuals. J Clin Invest 1993; 91:759–65.
6. Maggi E, Mazzetti M, Ravina A, et al. Ability of HIV to promote a TH1 to TH0 shift and to replicate preferentially in TH2 and TH0 cells [see comments]. Science 1994; 265:244–8.
7. Trinchieri G. Interleukin-12: a cytokine produced by antigen-presenting cells with immunoregulatory functions in the generation of T-helper cells type 1 and cytotoxic lymphocytes. Blood 1994; 84:4008–27.
8. Brunda M J, Luistro L, Warrier R R, et al. Antitumor and antimetastatic activity of interleukin 12 against murine tumors. J Exp Med 1993; 178:1223–30.
9. Scott P. IL-12: initiation cytokine for cell-mediated immunity. Science 1993; 260:496–7.
10. Clerici M, Lucey D R, Berzofsky J A, et al. Restoration of HIV-specific cell-mediated immune responses by interleukin-12 in vitro. Science 1993; 262:1721–4.
11. Voest E E, Kenyon B M, M S O R, Truitt G, R J D A, Folkman J. Inhibition of angiogenesis in vivo by interleukin 12. J Natl Cancer Inst 1995; 87:581–6.
12. Angiolillo A L, Sgadari C, Taub D D, et al. Human interferon-inducible protein 10 is a potent inhibitor of angiogenesis in vivo. J Exp Med 1995; 182:155–62.
13. Foli A, Saville M W, Baseler M W, Yarchoan R. Effects of the Th1 and Th2 stimulatory cytokines interleukin-12 and interleukin-4 on human immunodeficiency virus replication. Blood 1995; 85:2114–23.

TABLE 1

COMMON TOXICITY CRITERIA

| TOXICITY | GRADE | | | | |
| --- | --- | --- | --- | --- | --- |
| | 0 | 1 | 2 | 3 | 4 |
| WBC | $\geq 4.0$ | 3.0–3.9 | 2.0–2.9 | 1.0–1.9 | <1.0 |
| PLT | WNL | 75.0–normal | 50.0–74.9 | 25.0–49.9 | <25.0 |
| Hgb | WNL | 10.0–normal | 8.0–10.0 | 6.5–7.9 | <6.5 |
| Granulocytes/Bands | $\geq 2.0$ | 1.5–1.9 | 1.0–1.4 | 0.5–0.9 | <0.5 |
| Lymphocytes | $\geq 2.0$ | 1.5–1.9 | 1.0–1.4 | 0.5–.09 | <0.5 |
| Hemorrhage (clinical) | none | mild, no transfusion | gross, 1–2 units transfusion per episode | gross, 3–4 units transfusion per episode | massive, >-4 units transfusion per episode |
| Infection | none | mild | moderate | severe | life-threatening |
| Nausea | none | able to eat reasonable intake | intake significantly decreased but can eat | no significant intake | — |
| Vomiting | none | 1 episode in 24 hrs | 2–5 episodes in 24 hrs | 6–10 episodes in 24 hrs | >10 episodes in 24 hrs. or requiring parenteral support |
| Diarrhea | none | increase of 2–3 stools/day over pre-Rx | increase of 4–5 stools/day, or nocturnal stools, or moderate cramping | increase of 7–9 stools/day, or incontinence, or severe cramping | increase of $\geq 10$ stools/day, or grossly bloody diarrhea, or need for parenteral support |
| Stomatitis | none | painless ulcers, erythema, or mild soreness | painful erythema, edema, or ulcers, but can eat | painful erythema, edema, or ulcers, and cannot eat | requires parenteral or enteral support |
| Bilirubin | WNL | — | <1.5 × N | 1.5–3.0 × N | >3.0 × N |
| Transaminase (SGOT, SGPT) | WNL | $\leq 2.5 \times N$ | 2.6–5.0 × N | 5.1–20.0 × N | >20.0 × N |
| Alk Phos or 5' nucleotidase | WNL | $\leq 2.5 \times N$ | 2.6–5.0 × N | 5.1–20.0 × N | >20.0 × N |
| Liver (clinical) | no change from baseline | — | — | precoma | hepatic coma |
| Creatinine | WNL | <1.5 × N | 1.5–3.0 × N | 3.1–6.0 × N | >6.0 × N |
| Proteinuria | no change | 1+ or <0.3 g % or <3 g/l | 2–3+ or 0.3–1.0 g % or 3–10 g/l | 4+ or >1.0 g % or >10 g/l | nephrotic syndrome |
| Hematuria | neg | micro only | gross, no clots | gross + clots | requires transfusion |
| Alopecia | no loss | mild hair loss | pronounced or total hair loss | — | — |
| Pulmonary | none or no change | asymptomatic, with abnormality in PTFA | dyspnea on significant exertion | dyspnea at normal level of activity | dyspnea at rest |
| Cardiac dysrhythmias | none | asymptomatic, transient, requiring no therapy | recurrent or persistent, no therapy required | requires treatment | requires monitoring; or hypotension, or ventricular tachycardia, or fibrillation |

TABLE 1-continued

COMMON TOXICITY CRITERIA

| TOXICITY | GRADE | | | | |
|---|---|---|---|---|---|
| | 0 | 1 | 2 | 3 | 4 |
| Cardiac function | none | asymptomatic, decline of resting ejection fraction by less than 20% of baseline value | asymptomatic, decline of resting ejection fraction by more than 20% of baseline value | mild CHF, responsive to therapy | severe or refractory CHF |
| Cardiac-ischemia | none | non-specific T-wave flattening | asymptomatic, ST and T wave changes suggesting ischemia | angina without evidence for | acute myocardial infarction |
| Cardiac-pericardial | none | asymptomatic, effusion, no intervention required | pericarditis, rub. chest pain, ECG changes) | symptomatic effusion: drainage required | amponades drainage urgently required |
| Hypertension | none or no change | asymptomatic, transient increase by greater than 20 mm Hg (D) or to >150/100 if previosly WNL. No treatment required | recurrent or persistent increase by greater than 20 mm Hg (D) or to >150/100 if previously WNL. No treatment required | requires therapy | hypertensive crisis |
| Hypotension | none or no change | changes requiring no therapy (including transient orthostatic hypotension) | requires fluid replacement or other therapy but no hospitalization | requires therapy and hospitalization: resolves within 48 hrs of stopping the agent | requires therapy and hospitalization for >48 hrs after stopping the agent |
| Neuro-sensory | none or no change | mild paresthesias, loss of deep tendon reflexes | mild or moderate objective sensory loss: moderate paresthesias | severe objective sensory loss or paresthesias that interfere with function | — |
| Neuro-motor | none or no change | subjective weakness: no objective findings | mild objective weakness without significant impairment of function | objective weakness with impairment of function | paralysis |
| Neuro-cortical | none | mild somnoience or agitation | moderate somnoience or agitation | severe somnoience, agitation, confusion, disorientation, or hallucinations | coma, seizures, toxic psychosis |
| Neuro-cerebellar | none | slight incoorcination, dysdiadokinesis | intention tremor, dysmerna, slurred speech, hystagmus | locomotor ataxia | cerebellar necrosis |
| Neuro-mood | no change | mild anxiety or depression | moderate anxiety or depression | severe anxiety or depression | suicidal ideation |
| Neuro-headache | none | mild | moderate or sever but transient | unrelenting and severe | — |
| Neuro-constipation | none or no change | mild | moderate | severe | ileus >96 hrs |
| Neuro-hearing | none or no change | asymptomatic, hearing loss on audiometry only | tinnitus | hearing loss interfering with function but correctable with hearing aid | deafness not correctable |
| Neuro-vision | none or no change | — | — | symptomatic sub-local loss of vision | blindness |
| Skin | none or no change | scattered macular or papular eruption or erythema that is asymptomatic | scattered macular or papular eruption or erythema with pruritus or other associated eruption symptoms | generalized symptomatic macular, papular, or vesicular | exfoliative dermatitis or ulcerating dermatitis |
| Allergy | none | transient rash, drug fever <38 C., 100.4 F. | urticara, drug fever = 38 C., 100.4 F. mild bronchospasm | serum sickness, bronchospasm, req parenteral meds | anaphylaxis |
| Fever in absence of infection | none | 37.1–38.0 C. 98.7–100.4 F. | 38.1–40.0 C. 100.5–104.0 F. | >40.0 C. >104.0 F. for less than 24 hours | >40.0 C. (104.0 F.) for more than 24 hrs or fever accompanied by hypotension |
| Local | none | pain | pain and swelling, with inflammation or phlebitis | ulceration | plastic surgery indicated |

TABLE 1-continued

COMMON TOXICITY CRITERIA

| TOXICITY | GRADE | | | | |
|---|---|---|---|---|---|
| | 0 | 1 | 2 | 3 | 4 |
| Weight gain/loss | <5.0% | 5.0–9.9% | 10.0–19.9% | >20.0% | — |
| Hyperglycemia | <116 | 116–160 | 161–250 | 251–500 | >500 or ketoacidosis |
| Hypoglycemia | >64 | 55–64 | 40–54 | 30–39 | <30 |
| Amylase | WNL | <1.5 × N | 1.5–2.0 × N | 2.1–5.0 × N | >5.1 × N |
| Hypercalcemia | <10.6 | 10.5–11.5 | 11.6–12.5 | 12.6–13.5 | ≧13.5 |
| Hypocalcemia | >8.4 | 8.4–7.8 | 7.7–7.0 | 6.9–6.1 | ≦6.0 |
| Hypomagnesemia | >1.4 | 1.4–1.2 | 1.1–0.9 | 0.8–0.6 | ≦0.5 |
| Fibrinogen | WNL | 0.99–0.75 × N | 0.74–0.50 × N | 0.49–0.25 × N | ≦0.24 × N |
| Prothrombin time | WNL | 1.01–1.25 × N | 1.26–1.50 × N | 1.51–2.00 × N | >2.00 × N |
| Partial thromboplastin time | WNL | 1.01–1.66 × N | 1.67–2.33 × N | 2.34–3.00 × N | >3.00 × N |

AUTOLOGOUS BONE MARROW OR BLOOD STEM CELL SUPPORT STUDIES SUPPLEMENTARY TOXICITY CRITERIA
Grade 5 Death due to bacterial or fungal infection or hemorrhage associated with neutrophils <500/ul or platelets <10.000/ul more than 8 weeks after marrow transplantation.
Grade 4 Neutrophils <500/ul and/or platelets <10.000/ul for a duration in excess of 8 weeks.
Grade 3 Neutrophils <500/ul and/or platelets <10.000/ul for a duration of 4 to 8 weeks.
Grade 2 Neutrophils <500/ul and/or platelets <10.000/ul for a duration up to 4 weeks.
Grade 1 Neutropenia and/or thrombocytopenia, but neutrophils never <500/ul and platelets never <10.000/ul.
All other non-hematologic toxicities should be graded by the Common Toxicity Criteria.

What is claimed is:

1. A method of expressing IL-12 DNA in a mammalian subject, said method comprising administering to the subject a vector comprising DNA encoding IL-12 or a biologically active fragment or subunit thereof and expressing the IL-12 DNA in the subject, wherein the subject is suffering from Kaposi's sarcoma and wherein the vector is administered to a site of at least one lesion in the subject where IL-12 DNA expression is desired.

2. The method of claim 1, wherein the subject has Acquired Immune Deficiency Syndrome.

3. The method of claim 1, wherein the subject is a human being.

4. The method of claim 1, wherein the subject has a Kaposi's sarcoma lesion exhibiting angiogenesis.

5. The method of claim 1, wherein the biologically active fragment or subunit thereof encoded by the DNA has at least one of the following activities: reducing at least one Kaposi's sarcoma symptom, decreasing the number of lesion(s), decreasing the recurrence of lesion(s), decreasing the spread of lesion(s), decreasing the size of lesions(s), reducing angiogenesis in lesion(s), reducing the formation of new lesion(s).

6. A method of expressing IL-12 in at least one Kaposi's sarcoma cell, said method comprising administering to the cell a vector comprising DNA encoding IL-12 or a biologically active fragment or subunit thereof and allowing the cell to express IL-12.

7. The method of claim 6, wherein the biologically active fragment or subunit thereof encoded by the DNA has at least one of the following activities in the Kaposi's sarcoma cell:
(1) reducing the proliferation of the Kaposi's sarcoma cell;
(2) reducing the expression of at least one of basic fibroblast growth factor, vascular endothelial growth factor, platelet-derived growth factor, and interleukin-1; (3) increasing the expression of tissue inhibitor of metalloproteinase-2; (4) reducing the expression of proteins that enhance the proliferation or growth of the Kaposi's sarcoma cell; and (5) reducing the expression of at least one of basic fibroblast growth factor, vascular endothelial growth factor, platelet-derived growth factor, interleukin-1, scatter factor, and HIV-1 tat.

8. A method of expressing IL-12 DNA in a mammalian subject, said method comprising administering to the subject a vector comprising DNA encoding IL-12 or a biologically active fragment or subunit thereof and expressing the IL-12 DNA in the subject, wherein the subject is suffering from Kaposi's sarcoma and wherein the vector is administered to at least one Kaposi's sarcoma lesion.

9. The method of claim 8, wherein the subject has Acquired Immune Deficiency Syndrome.

10. The method of claim 8, wherein the subject is a human being.

11. The method of claim 8, wherein the subject has a Kaposi's sarcoma lesion exhibiting angiogenesis.

12. The method of claim 8, wherein the biologically active fragment or subunit thereof encoded by the DNA has at least one of the following activities: reducing Kaposi's sarcoma symptoms, decreasing the number of lesion(s), decreasing the recurrence of lesion(s), decreasing the spread of lesion (s), decreasing the size of lesions(s), reducing angiogenesis in lesion(s), reducing the formation of new lesion(s).

* * * * *

UNITED STATES PATENT AND TRADEMARK OFFICE
CERTIFICATE OF CORRECTION

PATENT NO. : 6,509,321 B1  
DATED : January 21, 2003  
INVENTOR(S) : Robert Yarchoan et al.

It is certified that error appears in the above-identified patent and that said Letters Patent is hereby corrected as shown below:

<u>Title page,</u>
Item [73], Assignee, should read as follows:

-- [73] Assignee: Genetics Institute, LLC., Cambridge, MA (US) --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,509,321 B1
DATED        : January 21, 2003
INVENTOR(S)  : Robert Yarchoan et al.

Page 1 of 1

It is certified that error appears in the above-identified patent and that said Letters Patent is hereby corrected as shown below:

<u>Title page,</u>
Item [73], Assignee, should read as follows:
-- Genetics Institute, LLC., Cambridge, MA (US); USA, DHHS., Rockville, MD (US) --.

Signed and Sealed this

Twenty-sixth Day of August, 2003

JAMES E. ROGAN
*Director of the United States Patent and Trademark Office*